United States Patent
Gerlach et al.

(10) Patent No.: US 12,269,795 B2
(45) Date of Patent: Apr. 8, 2025

(54) CANNABINOID EMULSIFIER

(71) Applicants: SYNERGY LIFE SCIENCE, Inc., Buford, GA (US); Ethox Chemicals, LLC, Greenville, SC (US)

(72) Inventors: Chris D. Gerlach, Buford, GA (US); Paul F. Sullivan, Greenville, SC (US); Charles F. Palmer, Jr., Greenville, SC (US); Andrew K. Tobias, Jr., Greenville, SC (US); Edward T. Borish, Greenville, SC (US); Brad P. Keown, Greenville, SC (US); Nora E. H. Bridenstine, Greenville, SC (US); James T. Tanner, Greenville, SC (US)

(73) Assignees: SYNERGY LIFE SCIENCE, Inc, Buford, GA (US); Ethox Chemicals, LLC, Greenville, SC (US)

( * ) Notice: Subject to any disclaimer, the term of this patent is extended or adjusted under 35 U.S.C. 154(b) by 192 days.

(21) Appl. No.: 17/527,465

(22) Filed: Nov. 16, 2021

(65) Prior Publication Data

US 2022/0153670 A1 May 19, 2022

Related U.S. Application Data

(60) Provisional application No. 63/114,010, filed on Nov. 16, 2020.

(51) Int. Cl.

| | | |
|---|---|---|
| C07C 43/285 | (2006.01) | |
| A61K 36/185 | (2006.01) | |
| A61K 47/08 | (2006.01) | |
| A61K 47/22 | (2006.01) | |
| A61P 29/00 | (2006.01) | |
| C07D 311/80 | (2006.01) | |

(52) U.S. Cl.
CPC .......... *C07C 43/285* (2013.01); *A61K 36/185* (2013.01); *A61K 47/08* (2013.01); *A61K 47/22* (2013.01); *A61P 29/00* (2018.01); *C07D 311/80* (2013.01)

(58) Field of Classification Search
None
See application file for complete search history.

(56) References Cited

U.S. PATENT DOCUMENTS

| | | | |
|---|---|---|---|
| 10,384,997 B2 * | 8/2019 | Kavarana | C12N 9/0004 |
| 2010/0273895 A1 | 10/2010 | Stinchcomb et al. | |
| 2015/0342902 A1 | 12/2015 | Vangara et al. | |
| 2018/0042845 A1 | 2/2018 | Sinai et al. | |
| 2019/0135225 A1 | 5/2019 | Kim | |

(Continued)

FOREIGN PATENT DOCUMENTS

| | | |
|---|---|---|
| WO | WO 2008107879 A1 | 9/2008 |
| WO | WO 2010/126501 A1 | 11/2010 |

(Continued)

OTHER PUBLICATIONS

Noriaki Bulletin of the Chemical Society of Japan 1962 35(6):1016-1020 (Year: 1962).*

(Continued)

*Primary Examiner* — Robert A Wax
*Assistant Examiner* — Caralynne E Helm
(74) *Attorney, Agent, or Firm* — Joseph T. Guy; Patent Filing Specialist Inc.

(57) ABSTRACT

Provided herein is a compound which is particularly suitable for use as a cannabinoid, as an emulsifier for a cannabinoid, in a formulation comprising the compound and in a method of treatment using the compound. The compound is defined by the General Formula:

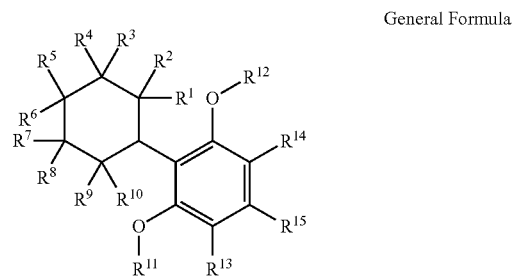

General Formula wherein:
$R^1$-$R^{10}$ are independently selected from H or an alkyl of 1-10 carbons; alkenyl of up to 10 carbons; or groups on adjacent carbons may be taken together to form an alkene;

$R^{11}$ and $R^{12}$ are independently H or —$(CH_2CHR^{16}O)_x$—$R^{17}$ with the proviso that at least one of $R^{11}$ or $R^{12}$ represents —$(CH_2CHR^{16}O)_xR^{17}$—; $R^{11}$ and $R^{10}$ may be taken together to represent —$C(R^{19})_2$—;

$R^{13}$-$R^{15}$ independently represent H or an alkyl of 1-8 carbons;

each $R^{16}$ independently represents H or an alkyl of 1-3 carbons;

each $R^{17}$ independently represents H, an alkyl or substituted alkyl of 1-22 carbons, aryl or substituted aryl or the ester of an acid;

each $R^{19}$ independently represents H or an alkyl of 1-5 carbons; and each x is independently an integer of 1-100.

70 Claims, No Drawings

(56) References Cited

U.S. PATENT DOCUMENTS

2019/0298683 A1    10/2019  Friedman
2022/0267239 A1 *  8/2022   Omeara ................ C07C 69/96

FOREIGN PATENT DOCUMENTS

WO    WO-2018175992 A1 *  9/2018  ........... A23L 33/105
WO    WO 2019135225        7/2019

OTHER PUBLICATIONS

Baswan et al. Clinical, Cosmetic and Investigational Dermatology 2020 13:927-942 (Year: 2020).*
Levinsohn et al. Journal of the Neurological Sciences 2020 411:116717:1-6 (Year: 2020).*
Zen "Extraction of cannabinoids using vegetable oils and its uva-photoprotective effect on human skin keratinocytes" Chulalongkorn University Theses and Dissertations (Chula ETD) 2021:4854 (Year: 2021).*
ISA/US; International Search Report and Written Opinion prepared for PCT/US2021/059476; Applicant: Synergy Life Science, Inc. et al.; Date mailed: May 4, 2022.

* cited by examiner

CANNABINOID EMULSIFIER

CROSS-REFERENCE TO RELATED APPLICATIONS

This application claims the priority of U.S. Provisional Application No. 63/114,010 filed Nov. 16, 2020 which is incorporated herein by reference.

FIELD OF THE INVENTION

The present invention is related to an improved cannabinoid emulsifier, particularly cannabidiol (CBD). More specifically, the present invention is related to an ethoxylated cannabinoid emulsifier which is particularly suitable for emulsifying cannabinoids and particularly CBD.

BACKGROUND

Cannabidiol (CBD) is an oily cannabinoid first discovered in Cannabis extracts in 1940. CBD is produced from the flowers, leaves, and stalks of the *Cannabis sativa* plant. CBD accounts for up to 40% of the plant extract but does not contain tetrahydrocannabinol (THC). This extract is frequently diluted with hemp seed oil, olive oil, or other types of carrier oils. CBD enriched oil products are non-psychoactive and typically contain ~20% CBD.

In 2012, Israeli scientists identified more than 1,200 human genes affected by CBD wherein 600 gene transcripts were upregulated by CBD and 524 were downregulated. CBD has also been shown to regulate the expression of 491 genes with 165 of the genes being in skin.

CBD, as most cannabinoids, has very low water solubility. Therefore, to incorporate CBD into a water-based formulations, such as cosmetic formulations, an emulsifier system must be used. The art contains a number of examples of CBD formulations. Relevant references are discussed herein.

US Publ. Appl. No. 2019298683, which is incorporated herein by reference, teaches a high concentration self-emulsifying formulation comprising: (i) about 20% to about 90% by weight of a cannabinoid or mixture of cannabinoids; (ii) about 5% to about 50% by weight of a terpene or terpene mixture, and (iii) about 5% to about 50% by weight of an emulsifier or emulsifier mixture. The teachings are specific to a pharmaceutical composition or mixture that self-emulsifies in an aqueous medium to produce a plurality of particles having an average particle size of about 100 microns to about 10 nm. The emulsifier includes polysorbate 80, oleoyl polyoxyl-6 glyceride, polyoxyl 35 hydrogenated castor oil, sucrose distearate, tocopherol polyethylene glycol 1000 succinate, lauroyl polyoxyl-32 glyceride, sorbitan monooleate, salts thereof and derivatives thereof.

US Publ. Appl. No. 20100273895, which is incorporate herein by reference, teaches cannabidiol formulations and methods of use. Specifically taught is a pharmaceutical composition comprising: (A) 1-10% (wt/wt) cannabidiol based on the composition; (B) 40% to 61% (wt/wt) ethanol relative to the composition; (C) 2.5% to 10% (wt/wt) diethylene glycol monoethyl ether relative to the composition; (D) 5% to 20% (wt/wt) propylene glycol based on the composition; (E) 0.1% to 3% (wt/wt) isopropyl myristate relative to the composition; and (f) an amount of water sufficient to bring the composition to a total of 100% (wt/wt).

US Publ. Appl. No. 2015342902, which is incorporated herein by reference, teaches specific cannabinoid formulations. Specifically taught is an oral pharmaceutical formulation comprising: cannabidiol and caprylic/capric triglyceride, wherein the formulation provides a greater cannabidiol Cmax, AUC(O-inf) and/or AUC (0-t) when administered to a subject in a fed condition than when administered to a subject in a fasted condition.

U.S. Publ. App. No. 20180042845, which is incorporated herein by reference, is specific to preparations of *cannabis* emulsions and methods thereof. More specifically taught is a composition comprising phospholipids, or derivatives thereof, and an oily fraction. The composition is formulated as an emulsion; wherein the oily fraction contains about 50% cannabinoids.

WO 2019135225A1, which is incorporated herein by reference, teaches solid self-emulsifying cannabinoid compositions. More specifically, the teachings are directed to a solid self-emulsifying cannabinoid composition, comprising: a) from about 0.1% to about 30% by weight of at least one cannabinoid or a mixture thereof, b) from about 1.0% to about 5% by weight of at least one essential oil or at least one terpene or a mixture thereof, c) from about 1% to about 40% of at least two emulsifiers, and d) from about 40% to about 90% of at least one adsorbing powder. At least one cannabinoid is essentially solubilized in the mixture of the at least one terpene, at least one essential oil and at least two emulsifiers. The resulting mixture is adsorbed onto the at least one adsorbing powder affording a solid self-emulsifying composition. The solid composition self emulsifies upon contact with water or mammal's body fluids to produce an oil-in-water sub-micron emulsion comprising a plurality of particles having a mean particle size of from about 10 nm to about 1,000 nm. WO 2019135225A1 also teaches that at least one of the emulsifiers is selected from non-ionic surfactants with HLB of about 10 to about 16 and the other(s) emulsifier is selected from non-ionic hydrophilic or hydrophobic surfactants having a HLB value of about 2 to about 12. WO 2019135225A1 also teaches that the hydrophilic emulsifier has an HLB from about 10 to about 16 and is selected from the group consisting of sucrose ester, sucrose stearate, sucrose laurate, sucrose oleate, polysorbate, polyoxyl hydrogenated castor oil, polyoxyl castor oil, tocopherol polyethylene glycol 1000 succinate, poly glyceryl fatty acid ester and combinations thereof and mixtures thereof, in a concentration of from about 1% w/w to about 20% w/w, preferably from about 2% w/w to about 10% w/w. WO 2019135225A1 also teaches that at least one emulsifier has an HLB from about 2 to about 12 and is selected from the group consisting of sorbitan fatty acid esters, sorbitan monooleate, sorbitan stearate, sorbitan oleate, sucrose ester, sucrose di and tri stearate, polyglyceryl fatty acid esters, polyglyceryl-3 dioleate, fatty acids esters and ethers, steareth-2, oleth-2, ceteth-2, salts thereof, derivatives thereof, and combinations thereof.

In spite of the extensive efforts, there is still a need for a better emulsifier for liquid cannabinoid, particularly CBD, formulations. The ideal emulsifier would be highly compatible with CBD, be nonionic in nature so it will be compatible with either anionic or cationic components in a skin care formulation, and be unaffected by the presence of water or other formulation components. An improved emulsifier, based on ethoxylated cannabinoids, is provided herein.

SUMMARY OF THE INVENTION

The present invention is related to an improved emulsifier which can provide the biological benefits of a cannabinoid.

A particular feature of the present invention is the ability to emulsify cannabinoids thereby providing for formulations, and particularly aqueous formulations, comprising cannabinoids.

These and other advantages, as will be realized, are provided in a compound defined by the General Formula:

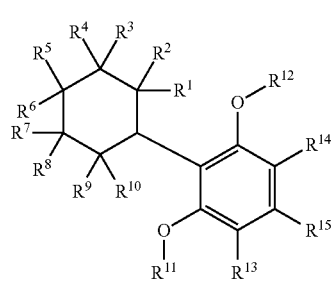

General Formula wherein:
R$^1$-R$^{10}$ are independently selected from H or an alkyl of 1-10 carbons; alkenyl of up to 10 carbons; or groups on adjacent carbons may be taken together to form an alkene; R$^{11}$ and R$^{12}$ are independently H or —(CH$_2$CHR$^{16}$O)$_x$—R$^{17}$ with the proviso that at least one of R$^{11}$ or R$^{12}$ represents —(CH$_2$CHR$^{16}$O)$_x$R$^{17}$—; R$^{11}$ and R$^{10}$ may be taken together to represent C(R$^{19}$)$_2$—;

R$^{13}$-R$^{15}$ independently represent H or an alkyl of 1-8 carbons;

each R$^{16}$ independently represents H or an alkyl of 1-3 carbons;

each R$^{17}$ independently represents H, an alkyl or substituted alkyl of 1-22 carbons, aryl or substituted aryl or the ester of an acid;

each R$^{19}$ independently represents H or an alkyl of 1-5 carbons; and each x is independently an integer of 1-100.

Yet another embodiment is provide in formulation comprising: a compound defined by General Formula:

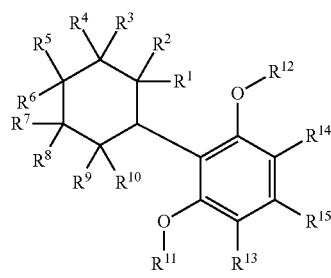

General Formula wherein:
R$^1$-R$^{10}$ are independently selected from H or an alkyl of 1-10 carbons; alkenyl of up to 10 carbons; or groups on adjacent carbons may be taken together to form an alkene;

R$^{11}$ and R$^{12}$ are independently H or —(CH$_2$CHR$^{16}$O)$_x$—R$^{17}$ with the proviso that at least one of R$^{11}$ or R$^{12}$ represents —(CH$_2$CHR$^{16}$O)$_x$R$^{17}$—; R$^{11}$ and R$^{10}$ may be taken together to represent C(R$^{19}$)$_2$—;

R$^{13}$-R$^{15}$ independently represent H or an alkyl of 1-8 carbons;

each R$^{16}$ independently represents H or an alkyl of 1-3 carbons;

each R$^{17}$ independently represents H, an alkyl or substituted alkyl of 1-22 carbons, aryl or substituted aryl or the ester of an acid;

each R$^{19}$ independently represents H or an alkyl of 1-5 carbons; and each x is independently an integer of 1-100; and a cannabinoid.

Yet another embodiment is provided in a method for treating tissue comprising applying a formulation comprising:

a compound defined by General Formula:

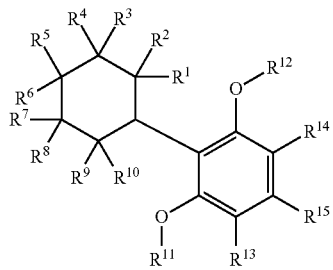

General Formula wherein:
R$^1$-R$^{10}$ are independently selected from H or an alkyl of 1-10 carbons; alkenyl of up to 10 carbons; or groups on adjacent carbons may be taken together to form an alkene;

R$^{11}$ and R$^{12}$ are independently H or —(CH$_2$CHR$^{16}$O)$_x$—R$^{17}$ with the proviso that at least one of R$^{11}$ or R$^{12}$ represents —(CH$_2$CHR$^{16}$O)$_x$R$^{17}$—; R$^{11}$ and R$^{10}$ may be taken together to represent C(R$^{19}$)$_2$—;

R$^{13}$-R$^{15}$ independently represent H or an alkyl of 1-8 carbons;

each R$^{16}$ independently represents H or an alkyl of 1-3 carbons;

each R$^{17}$ independently represents H, an alkyl or substituted alkyl of 1-22 carbons, aryl or substituted aryl or the ester of an acid;

each R$^{19}$ independently represents H or an alkyl of 1-5 carbons; and each x is independently an integer of 1-100; and a cannabinoid.

DESCRIPTION

The instant invention is specific to an emulsifier which is the poly(alkyleneoxide) ethers of cannabinoids, represented by the General Formula. The emulsifier is formed from the reaction of preferably, ethylene oxide (EO) or propylene oxide (PO) with a cannabinoid and particularly CBD. The resulting emulsifier is nonionic in character. Depending on the ratio of EO and PO to CBD, as a representative cannabinoid, the water solubility can be adjusted higher or lower. More EO will make the resulting emulsifier more water soluble and adjust its emulsifying power. Using CBD as the representative hydrophobe of the emulsifier ensures excellent compatibility with the native compound or free CBD oil. The ether linkages of the emulsifier are resistant to hydrolysis and thus the emulsifier is indefinitely stable in water and in the presence of other formulation components.

The emulsifier is represented by General Formula:

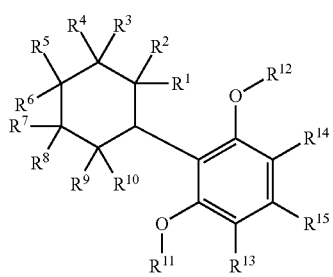

General Formula wherein:
R$^1$-R$^{10}$ are independently selected from H or an alkyl of 1-10 carbons; alkenyl of up to 10 carbons; or groups on adjacent carbons may be taken together to form an alkene; R$^1$, R$^5$, R$^6$, R$^7$, R$^8$ and R$^9$ are preferably H; R$^2$ and R$^3$ are preferably taken together to form an alkene; R$^4$ is preferably —CH$_3$; R$^{10}$ is preferably —C(=CH$_2$)CH$_3$;

R$^{11}$ and R$^{12}$ are independently H or —(CH$_2$CHR$^{16}$O)$_x$—R$^{17}$ with the proviso that at least one of R$^{11}$ or R$^{12}$ represents —(CH$_2$CHR$^{16}$O)$_x$R$^{17}$—; R$^{11}$ and R$^{10}$ may be taken together to represent C(R$^{19}$)$_2$—;

R$^{13}$-R$^{15}$ independently represent H or an alkyl of 1-8 carbons; R$^{13}$ and R$^{14}$ are preferably H; R$^{15}$ is preferably an alkyl of 1-8 carbons and more preferably —(CH$_2$)$_4$CH$_3$;

each R$^{16}$ independently represents H or an alkyl of 1-3 carbons; each R$^{16}$ preferably independently represents H or —CH$_3$;

each R$^{17}$ independently represents H, an alkyl or substituted alkyl of 1-22 carbons, aryl or substituted aryl; alternatively R$^{17}$ is the ester of an acid, —C(O)—R$^{18}$, wherein each R$^{18}$ preferably represents the remnant of an acid or ester preferably salicylic acid, methyl salicylate, a carboxylic acid of 5 to 10 carbons, cinnamic acid, citric acid, retinoic acid, and ascorbic acid. In an embodiment R$^{18}$ represents the remnant of a C1-C22 organic acid or ester wherein C1-C22 represents 1-22 carbons which are preferably alkyl carbons.

each R$^{19}$ independently represents H or an alkyl of 1-5 carbons; each R$^{19}$ is preferably —CH$_3$;

each x is independently an integer of 1-100 and preferably 3-13.

A particularly preferred emulsifier of the General Formula is represented by Formula I:

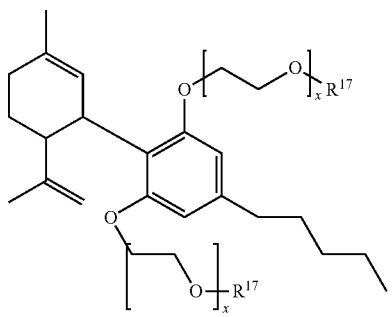

Formula I

In a particularly preferred embodiment of Formula I, each x is independently 3-13 and each R$^{17}$ is independently selected from H, C(O)C$_6$H$_4$OH, —C(O)CH=CHC$_6$H$_6$, —C(O)(CH$_2$)$_7$CH$_3$, or —C(O)(CH$_2$)$_9$CH$_3$ and preferably both R$^{17}$ groups are the same.

Another particularly preferred embodiment of the General Formula is represented by Formula II:

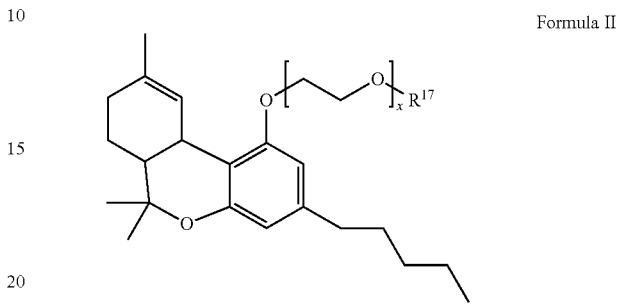

Formula II

In a particularly preferred embodiment of Formula II, each x is independently 3-13 and each R$^{17}$ is independently selected from H, C(O)C$_6$H$_4$OH, —C(O)CH=CHC$_6$H$_5$, —C(O)(CH$_2$)$_7$CH$_3$, or —C(O)(CH$_2$)$_9$CH$_3$ and preferably both R$^{17}$ groups are the same.

For substituent —C(O)—R$^{18}$, each R$^{18}$ preferably represents the remnant of an acid or ester. By way of a clarifying non-limiting example, for an acid or ester, generally represented by R—C(O)OX wherein X is H or an alkyl, R$^{18}$ would be the remnant, R, remaining after esterification. Particularly preferred acids or esters include salicylic acid or methyl salicylate wherein R$^{17}$ is —C(O)C$_6$H$_4$OH, a carboxylic acid of 6 to 10 carbons wherein R$^{17}$ is —C(O)(CH$_2$)$_{5-9}$CH$_3$ or cinnamic acid wherein R$^{17}$ is —C(O)CH=CHC$_6$H$_5$. Other acids or ester suitable for demonstration of the invention are C1-C22 organic carboxylic acids.

The ether groups, —(CH$_2$CHR$^{16}$O)$_x$R$^{17}$—, alter the hydrophilic-lipophilic balance (HLB) of the emulsifier with a higher number of —CH$_2$CHR$^{16}$O— groups being consistent with a higher HLB. An HLB of at least 8 is preferred with and HLB of 12-16 being more preferred.

The emulsifier is particularly suitable for emulsifying cannabinoid in a formulation and particularly an aqueous formulation comprising cannabinoids. Cannabinoids are marginally soluble, if soluble at all, in aqueous solutions and the instant emulsifier allows the cannabinoid to be utilized in an aqueous formulation. A preferred formulation comprises at least 1 wt % to 99 w % emulsifier with the balance being selected from solvents, oils, surfactants, cannabinoid.

A preferred solvent is water with other solvents being suitable for demonstration of the invention. Other suitable solvents include alcohols.

Oils, particularly natural oils or their alkyl esters, are particularly suitable for use with the invention. Particularly suitable oils include glycerides such as monoglycerides, diglycerides and particularly triglycerides. Particularly preferred oils include coconut oil, olive oil and hempseed oil.

The emulsifier is particularly suitable for use in a cosmeceutical for use in acne regulation, cell renewal and regeneration, epidermal barrier formulations, extracellular matrix integrity formulations, pigmentation regulation or melanogenesis, for skin hydration, tissue remodeling, wound healing, insulin signaling, pain treatment, inflammation mitigation, immune response, circadian rhythm treatments, antioxidant stress relief, CB1 partial agonist, emollient or humectant, skin brightening, as a barrier cream, as a skin protectant, and as a sun protection factor (SPF) enhancer, as a film former, or as a fragrance fixative.

A particularly preferred formulation comprises the emulsifier and a cannabinoid obtained from cannabis. Particularly preferred cannabinoids are selected from the group consisting of CBD, THC, cannabichromene (CBC), cannabichromevarin (CBCV), cannabidiphorol (CBDP), cannabidivarinic acid (CBDVA), cannabielsoin (CBEA), cannabigerolic acid (CBCA), cannabigerolic acid monomethyl ether (CBGAM), cannabigerovarinic acid (CBGVA), cannabicyclolic acid (CBLA), cannabinolic acid (CBNA), cannabicitranic acid (CBTA), cannabivarinic acid (CBVA), tetrahydrocannabinolic acid (THCA), tetrahydrocannabiorcolic acid (THCCA), tetrahydrocannabiphorolic acid (THCPA), tetrahydrocannabinolic acid (THCA), tetrahydrocannabivarinic acid (THCVA), cannadibiphorol (CBDP), cannabidivarin (CBDV), cannabielsoin (CBE), cannabigerol (CBG), cannabigerol monomethylether (CBGM), cannabigerovarin (CBG), cannabigerol monomethylether (CBGM), cannabigerovarin (CBGV), cannabicyclol (CBL), cannabinol (CBN), cannabicitran (CBTC), cannabivarin (CBV), tetrahydrocannabiorcol (THCC), tetrahydrocannabiphorol (THCP) or tetrahydrocannabivarin (TNCV). Other products from *cannabis* may be used in combination with the emulsifier such as hemp.

The emulsifier is specifically suitable for use in treating tissue, and particularly skin applications and oral applications wherein a formulation is applied to the skin or administered orally. A preferred formulation comprises water, a compound of the General Formula, a cannabinoid with cannabidiol or tetrahydrocannabinol being particularly preferred, and optional additives such as surfactants, emollients, lubricants, fragrances, colorants, flavorants, medications and the like.

The method of applying the formulation is not limited herein. The formulation may be applied by spraying, dripping, dipping or pouring the formulation onto the tissue to be treated. Alternatively, the formulation may be applied by an applicator such as by painting or wiping.

While not limited to theory, it is hypothesized that the emulsifier has similar biological activity to the native compound. For the purposes of this invention, the term native compound refers to a compound of the General Formula wherein $R^{11}$ and $R^{12}$ are H. By way of example, Formula I with x being zero and $R^{17}$ being H is CBD and Formula II with x being zero and $R^{17}$ being H is THC. By increasing the hydrophilicity of the native compound, to form the emulsifier, the emulsifier is better able to cross various mucosal membranes or the blood-brain barrier, thereby altering the biological effect. The emulsifier is therefore suitable to be used alone or the emulsifier can be used in combination with the native compound or a different cannabinoid.

The method of forming the emulsifier is not particularly limited with each step being well within the range of knowledge of those of skill in the art. The polyether groups are formed by typical ring opening reaction of ethylene oxide, or a derivative, in the presence of a catalyst as is well known in the art. The formation of the ester by the reaction of an alcohol and carboxylic acid is well known chemistry which is very familiar to those of skill in the art.

EXAMPLES

General Reaction Scheme

The esterification of CBD ethoxylate, as a representative cannabinoid, was conducted with a nitrogen sparge at elevated temperatures 170° C.). Two catalysts were employed for these reactions, either hypophosphorous acid, particularly for cinnamate and capric/caprylate, or titanium (IV) butoxide, particularly for salicylate. CBD has two free hydroxyls, which were ethoxylated and subsequently esterified. Therefore, the reactions were conducted in a 2:1 molar ratio, with the acid to be esterified in excess. It should be noted that the salicylate ester was prepared via transesterification with methyl salicylate, producing methanol as a by-product. One of skill in the art would realize the adjustments in molar ratios and conditions for other cannabinoids and acids.

Synthesis of Cinnamate-ester of CBD Ethoxylate

The reaction was conducted in a 3000 mL reaction flask, equipped with a heating mantle, temperature probe, overhead agitation, nitrogen sparge and a condenser. For a typical reaction, 1,279 g of CBD ethoxylate, 719 g trans-cinnamic acid and 2.0 g of hypophosphorous acid were added to the reaction flask. Under agitation and nitrogen sparge, the reaction was heated to 220° C. and held under constant agitation overnight. The reaction was then cooled to room temperature.

Synthesis of Caprate/Caprylate-ester of CBD Ethoxylate

The reaction was conducted in a 3000 mL reaction flask, equipped with a heating mantle, temperature probe, overhead agitation, nitrogen sparge and a condenser. For a typical reaction, 1,575 g of CBD ethoxylate, 922 g Capric/Caprylic acid and 2.5 g of hypophosphorous acid were added to the reaction flask. Under agitation and nitrogen sparge, the reaction was heated to 190° C. and held, under constant agitation overnight. The reaction was then cooled to room temperature.

Synthesis of Salicylate-ester of CBD Ethoxylate

The reaction was conducted in a 3000 mL reaction flask, equipped with a heating mantle, temperature probe, overhead agitation, nitrogen sparge and a condenser. For a typical reaction, 1,208 g (2.1 moles) of CBD ethoxylate, 791 g methyl salicylate (5.2 moles) and 1.0 g of titanium (IV) butoxide were added to the reaction flask. Under agitation and nitrogen sparge, the reaction was heated to 170° C. and held under constant agitation overnight. The reaction was then cooled to room temperature.

Synthesis of Retinoate-ester of CBD Ethoxylate

The reaction would be conducted in a 3000 mL reaction flask, equipped with a heating mantle, temperature probe, overhead agitation, nitrogen sparge and a condenser. For a typical reaction, 1,208 g (2.1 moles) of CBD ethoxylate, 1,352 g retinoic acid (4.5 moles) and 2.5 g of hypophosphorous acid would be added to the reaction flask. Under agitation and nitrogen sparge, the reaction would be heated to 170° C. and held, under constant agitation overnight. The reaction would then be cooled to room temperature.

Synthesis of Citrate-ester of CBD Ethoxylate

The reaction would be conducted in a 3000 mL reaction flask, equipped with a heating mantle, temperature probe, overhead agitation, nitrogen sparge and a condenser. For a typical reaction, 1,208 g (2.1 moles) of CBD ethoxylate, 864 g citric acid (4.5 moles) and 2.5 g of hypophosphorous acid would be added to the reaction flask. Under agitation and nitrogen sparge, the reaction would be heated to 170° C. and held, under constant agitation overnight. The reaction would then be cooled to room temperature.

Example 1

300 g of CBD isolate was charged to a pressure vessel and 0.1% KOH catalyst was added. After removing all water and air, the mixture was heated to 110-120° C. and 900 g of ethylene oxide (EO) was added over 7-8 hours. After EO addition was complete, the reactor was held at temperature until all of the EO was consumed. Trace EO and 1,4-dioxane were then removed using vacuum. The reactor contents were cooled and acetic acid was added to neutralize the catalyst and bring the pH into the 6-7 range. The resulting product was polyoxyethylene (21) CBD.

Example 2

10 g of CBD and 1.5 g of the product obtained by Example 1 were combined and the mixture added to 90 g of water with stirring. The CBD was emulsified and formed a clear emulsion.

Example 3

A first vessel was charged with deionized water (88.0 wt %), caprylyl glycol (1.0 wt %) and CannaSorb CBD-Active (1.0 wt %) followed by heating to 80° C. A second vessel was charged with Cannasorb LC (1.5 wt %) and Cannasol CBD-S (1.5 wt %) followed by heating to 80° C. with mixing until uniform. Using a homomixer at slow spead the components of the first vessel were added to the second vessel resulting in a lotion which thickened with increased addition of the water phase. The lotion was cooled to 35° C. followed by addition of a mixture of an Essential Oil Blend (0.3 wt %) comprising Eucalyptus Oil, Thyme Oil and Rosemary Oil and Vitacon ACE (0.2 wt %) comprising Vitamins A, C and E to obtain a formulation. Caprylyl glycol was obtained from Inolex. CannaSorb CBD-Active, Cannasorb LC and Cannasol CBD-S were obtained from Synergy Life Sciences Inc. The essential oil blend was obtained from Essential Ingredients Inc.

The formulation of Example 3 provided reduced pain and inflammation while providing skin rejuvenation.

The invention has been described with reference to preferred embodiments without limit thereto. One of skill in the art would realize additional embodiments which are described and set forth in the claims appended hereto.

The invention claimed is:

1. A compound defined by the General Formula:

General Formula

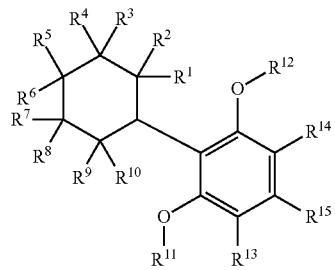

wherein:
R$^1$-R$^{10}$ are independently selected from H or an alkyl of 1-10 carbons; alkenyl of up to 10 carbons; or groups on adjacent carbons may be taken together to form an alkene;
R$^{11}$ represents —(CH$_2$CHR$^{16}$O)$_x$—R$^{17}$ or R$^{11}$ and R$^{10}$ may be taken together to represent C(R$^{19}$)$_2$—;
R$^{12}$ represents —(CH$_2$CHR$^{16}$O)$_x$—R$^{17}$;
R$^{13}$-R$^{15}$ independently represent H or an alkyl of 1-8 carbons;

each R$^{16}$ independently represents H or an alkyl of 1-3 carbons;
each R$^{17}$ independently represents H, an alkyl or substituted alkyl of 1-22 carbons, aryl or substituted aryl or the ester of an acid;
each R$^{19}$ independently represents H or an alkyl of 1-5 carbons; and
each x is independently an integer of 1-100.

2. The compound of claim 1 wherein R$^1$, R$^5$, R$^6$, R$^7$, R$^8$ and R$^9$ are H.

3. The compound of claim 1 wherein R$^2$ and R$^3$ are taken together to form an alkene.

4. The compound of claim 1 wherein R$^4$ is —CH$_3$.

5. The compound of claim 1 wherein R$^{10}$ is —C(CH$_2$)CH$_3$.

6. The compound of claim 1 wherein R$^{13}$ and R$^{14}$ are H.

7. The compound of claim 1 wherein R$^{15}$ is an alkyl of 1-8 carbons.

8. The compound of claim 7 wherein R$^{15}$ is —(CH$_2$)$_4$CH$_3$.

9. The compound of claim 1 wherein each R$^{16}$ independently represents H or —CH$_3$.

10. The compound of claim 1 wherein each R$^{19}$ is —CH$_3$.

11. The compound of claim 1 wherein each x is independently an integer of 3-13.

12. A compound defined by Formula I:

Formula I

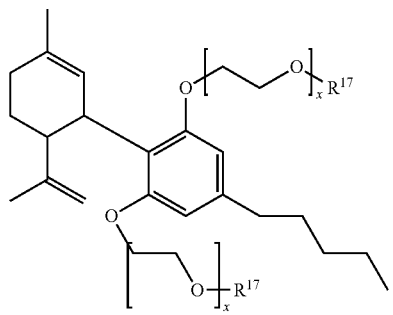

wherein each R$^{17}$ independently represents H, an alkyl or substituted alkyl of 1-22 carbons, aryl or substituted aryl or the ester of an acid; and
each x is independently an integer of 1-100.

13. The compound of claim 12 wherein each x is independently 3-13 and each R$^{17}$ is independently selected from H, C(O)C$_6$H$_4$OH, —C(O)CH=CHC$_6$H$_5$, —C(O)(CH$_2$)$_7$CH$_3$, or —(O)(CH$_2$)$_9$CH$_3$.

14. The compound of claim 13 wherein both R$^{17}$ groups are the same.

15. The compound of claim 12 wherein R$^{17}$ is the ester of an acid and has the structure C(O)R$^{18}$ wherein R$^{18}$ represents the remnant of the acid.

16. The compound of claim 15 wherein R$^{18}$ represents the remnant of salicylic acid, a carboxylic acid of 5 to 10 carbons, cinnamic acid, citric acid, retinoic acid, acetic acid, ascorbic acid, capric acid, or caprylic acid.

17. The compound of claim 1 wherein said compound is defined by Formula II:

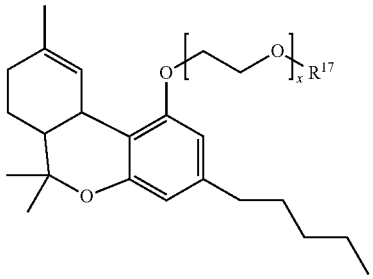

Formula II

18. The compound of claim 17 wherein x is 3-13 and $R^{17}$ is selected from H, $C(O)C_6H_4OH$, $-C(O)CH=CHC_6H_5$, $-C(O)(CH_2)_7CH_3$ or $-(O)(CH_2)_9CH_3$.

19. The compound of claim 1 having an HLB of at least 8.

20. The compound of claim 19 wherein said HLB of 12-16.

21. A formulation comprising:
a compound defined by General Formula:

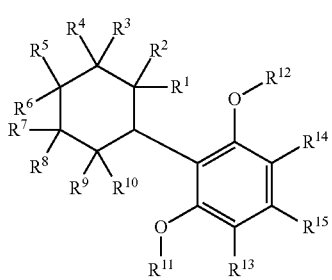

General Formula wherein:
$R^1$-$R^{10}$ are independently selected from H or an alkyl of 1-10 carbons; alkenyl of up to 10 carbons; or groups on adjacent carbons may be taken together to form an alkene;
$R^{11}$ represents $-(CH_2CHR^{16}O)_x-R^{17}$ or $R^{11}$ and $R^{10}$ may be taken together to represent $C(R^{19})_2$;
$R^{12}$ represents $-(CH_2CHR^{16}O)_x-R^{17}$;
$R^{13}$-$R^{15}$ independently represent H or an alkyl of 1-8 carbons;
each $R^{16}$ independently represents H or an alkyl of 1-3 carbons;
each $R^{17}$ independently represents H, an alkyl or substituted alkyl of 1-22 carbons, aryl or substituted aryl or the ester of an acid;
each $R^{19}$ independently represents H or an alkyl of 1-5 carbons; and
each x is independently an integer of 1-100; and
a cannabinoid.

22. The formulation of claim 21 wherein $R^1$, $R^5$, $R^6$, $R^7$, $R^8$ and $R^9$ are H.

23. The formulation of claim 21 wherein $R^2$ and $R^3$ are taken together to form an alkene.

24. The formulation of claim 21 wherein $R^4$ is $-CH_3$.

25. The formulation of claim 21 wherein $R^{10}$ is $-C(CH_2)CH_3$.

26. The formulation of claim 21 wherein $R^{13}$ and $R^{14}$ are H.

27. The formulation of claim 21 wherein $R^{15}$ is an alkyl of 1-8 carbons.

28. The formulation of claim 27 wherein $R^{15}$ is $-(CH_2)_4CH_3$.

29. The formulation of claim 21 wherein each $R^{16}$ independently represents H or $-CH_3$.

30. The formulation of claim 21 wherein each $R^{19}$ is $-CH_3$.

31. The formulation of claim 21 wherein each x is independently an integer of 3-13.

32. The formulation of claim 21 wherein said compound is defined by Formula II:

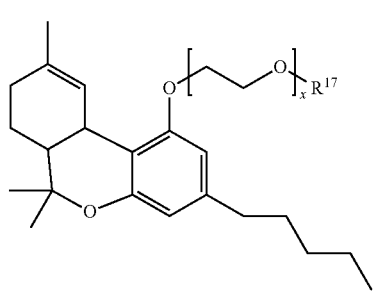

Formula II

33. The formulation of claim 32 wherein x is 3-13 and $R^{17}$ is selected from H, $C(O)C_6H_4OH$, $-C(O)CH=CHC_6H_5$, $-C(O)(CH_2)_7CH_3$, or $-(O)(CH_2)_9CH_3$.

34. The formulation of claim 21 wherein said compound has an HLB of at least 8.

35. The formulation of claim 34 wherein said HLB is 12-16.

36. The formulation of claim 21 further comprising water.

37. The formulation of claim 21 comprising hemp.

38. The formulation of claim 21 further comprising at least one additive selected from the group consisting of surfactants, emollients, lubricants, fragrances, colorants, flavorants, medications and natural oils.

39. The formulation of claim 38 further comprising at least one additive selected from the group consisting of coconut oil, olive oil, monoglycerides, diglycerides and triglycerides.

40. A formulation comprising a compound defined by Formula I:

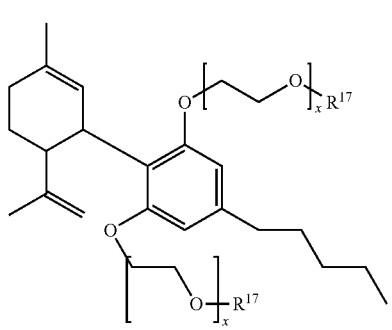

Formula I wherein each $R^{17}$ independently represents H, an alkyl or substituted alkyl of 1-22 carbons, aryl or substituted aryl or the ester of an acid; and each x is independently an integer of 1-100.

41. The formulation of claim 40 wherein each x is independently 3-13 and each $R^{17}$ is independently selected from H, $C(O)C_6H_4OH$, $-C(O)CH=CHC_6H_5$, $-C(O)(CH_2)_7CH_3$, or $-(O)(CH_2)_9CH_3$.

42. The formulation of claim 41 wherein both $R^{17}$ groups are the same.

43. The compound of claim 40 wherein $R^{17}$ is the ester of an acid and has the structure $C(O)R^{18}$ wherein $R^{18}$ represents the remnant of the acid.

44. The compound of claim 43 wherein $R^{18}$ represents the remnant of salicylic acid, a carboxylic acid of 5 to 10 carbons, cinnamic acid, citric acid, retinoic acid, acetic acid, ascorbic acid, capric acid, or caprylic acid.

45. A formulation comprising:
a compound defined by General Formula:

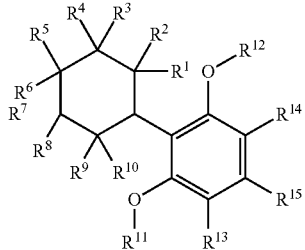

General Formula

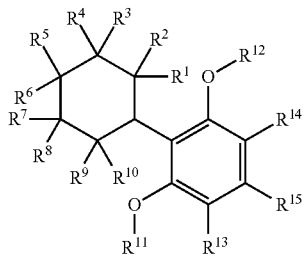

General Formula wherein:
- $R^1$-$R^{10}$ are independently selected from H or an alkyl of 1-10 carbons; alkenyl of up to 10 carbons; or groups on adjacent carbons may be taken together to form an alkene;
- $R^{11}$ and $R^{12}$ are independently $-(CH_2CHR^{16}O)_xR^{17}-$; $R^{11}$ and $R^{10}$ may be taken together to represent $C(R^{19})_2$—;
- $R^{13}$-$R^{15}$ independently represent H or an alkyl of 1-8 carbons;
- each $R^{16}$ independently represents H or an alkyl of 1-3 carbons;
- each $R^{17}$ independently represents H, an alkyl or substituted alkyl of 1-22 carbons, aryl or substituted aryl or the ester of an acid;
- each $R^{19}$ independently represents H or an alkyl of 1-5 carbons; and
- each x is independently an integer of 1-100; and
- a cannabinoid wherein said cannabinoid is selected from the group consisting of cannabidiol (CBD), tetrahydrocannabinol (THC), cannabichromene (CBC), cannabichromevarin (CBCV), cannabidiphorol (CBDP), cannabidivarinic acid (CBDVA), cannabielsoin (CBEA), cannabigerolic acid (CBCA), cannabigerolic acid monomethyl ether (CBGAM), cannabigerovarinic acid (CBGVA), cannabicyclolic acid (CBLA), cannabinolic acid (CBNA), cannabicitranic acid (CBTA), cannabivarinic acid (CBVA), tetrahydrocannabinolic acid (THCA), tetrahydrocannabiorcolic acid (THCCA), tetrahydrocannabiphorolic acid (THCPA), tetrahydrocannabivarinic acid (THCVA), cannabidivarin (CBDV), cannabielsoin (CBE), cannabigerol (CBG), cannabigerol monomethylether (CBGM), cannabigerovarin (CBGV), cannabicyclol (CBL), cannabinol (CBN), cannabicitran (CBTC), cannabivarin (CBV), tetrahydrocannabiorcol (THCC), tetrahydrocannabiphorol (THCP) and tetrahydrocannabivarin (TNCV).

46. A method for treating tissue comprising applying a formulation comprising: a compound defined by General Formula:

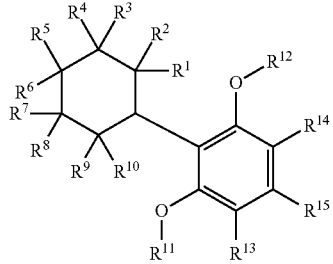

General Formula wherein:
- $R^1$-$R^{10}$ are independently selected from H or an alkyl of 1-10 carbons; alkenyl of up to 10 carbons; or groups on adjacent carbons may be taken together to form an alkene;
- $R^{11}$ and $R^{12}$ are independently $-(CH_2CHR^{16}O)_xR^{17}-$; $R^{11}$ and $R^{10}$ may be taken together to represent $C(R^{19})_2$;
- $R^{13}$-$R^{15}$ independently represent H or an alkyl of 1-8 carbons;
- each $R^{16}$ independently represents H or an alkyl of 1-3 carbons;
- each $R^{17}$ independently represents H, an alkyl or substituted alkyl of 1-22 carbons, aryl or substituted aryl or the ester of an acid;
- each $R^{19}$ independently represents H or an alkyl of 1-5 carbons; and
- each x is independently an integer of 1-100; and
- a cannabinoid.

47. The method for treating tissue of claim 46 wherein $R^1$, $R^5$, $R^6$, $R^7$, $R^8$ and $R^9$ are H.

48. The method for treating tissue of claim 46 wherein $R^2$ and $R^3$ are taken together to form an alkene.

49. The method for treating tissue of claim 46 wherein $R^4$ is $-CH_3$.

50. The method for treating tissue of claim 46 wherein $R^{10}$ is $-C(CH_2)CH_3$.

51. The method for treating tissue of claim 46 wherein $R^{13}$ and $R^{14}$ are H.

52. The method for treating tissue of claim 46 wherein $R^{15}$ is an alkyl of 1-8 carbons.

53. The method for treating tissue of claim 52 wherein $R^{15}$ is $-(CH_2)_4CH_3$.

54. The method for treating tissue of claim 46 wherein each $R^{16}$ independently represents H or $-CH_3$.

55. The compound of claim 46 wherein $R^{17}$ is the ester of an acid and has the structure $C(O)R^{18}$ wherein $R^{18}$ represents the remnant of the acid.

56. The compound of claim 55 wherein $R^{18}$ represents the remnant of salicylic acid, a carboxylic acid of 5 to 10 carbons, cinnamic acid, citric acid, retinoic acid, acetic acid, ascorbic acid, capric acid, or caprylic acid.

57. The method for treating tissue of claim 46 wherein each $R^{19}$ is —$CH_3$.

58. The method for treating tissue of claim 46 wherein each x is independently an integer of 3-13.

59. The method for treating tissue of claim 46 wherein said compound is defined by Formula I:

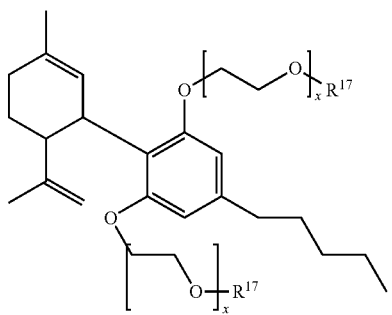

Formula I wherein
each x is independently an integer of 1-100; and
each $R^{17}$ independently represents H, an alkyl or substituted alkyl of 1-22 carbons, aryl or substituted aryl or the ester of an acid.

60. The method for treating tissue of claim 59 wherein each x is 3-13 and each $R^{17}$ is independently selected from H, $C(O)C_6H_4OH$, —$C(O)CH=CHC_6H_5$, —$C(O)(CH_2)_7CH_3$, or —$(O)(CH_2)_9CH_3$.

61. The method for treating tissue of claim 60 wherein both $R^{17}$ groups are the same.

62. The method for treating tissue of claim 46 wherein said compound is defined by Formula II:

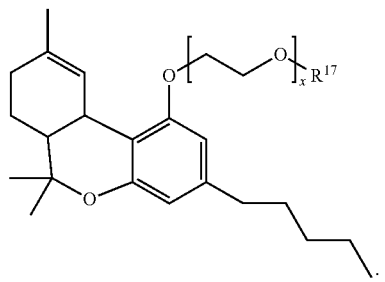

Formula II

63. The method for treating tissue of claim 62 wherein x is 3-13 and $R^{17}$ is selected from H, $C(O)C_6H_4OH$, —$C(O)CH=CHC_6H_5$ or —$C(O)(CH_2)_7CH_3$.

64. The method for treating tissue of claim 46 wherein said compound has an HLB of at least 8.

65. The method for treating tissue of claim 64 wherein said HLB is 12-16.

66. The method for treating tissue of claim 46 further comprising water.

67. The method for treating tissue of claim 46 wherein said cannabinoid is selected from the group consisting of cannabidiol (CBD), tetrahydrocannabinol (THC), cannabichromene (CBC), cannabichromevarin (CBCV), cannabidiphorol (CBDP), cannabidivarinic acid (CBDVA), cannabielsoin (CBEA), cannabigerolic acid (CBCA), cannabigerolic acid monomethyl ether (CBGAM), cannabigerovarinic acid (CBGVA), cannabicyclolic acid (CBLA), cannabinolic acid (CBNA), cannabicitranic acid (CBTA), cannabivarinic acid (CBVA), tetrahydrocannabinolic acid (THCA), tetrahydrocannabiorcolic acid (THCCA), tetrahydrocannabiphorolic acid (THCPA), tetrahydrocannabivarinic acid (THCVA), cannabidivarin (CBDV), cannabielsoin (CBE), cannabigerol (CBG), cannabigerol monomethylether (CBGM), cannabigerovarin (CBGV), cannabicyclol (CBL), cannabinol (CBN), cannabicitran (CBTC), cannabivarin (CBV), tetrahydrocannabiorcol (THCC), tetrahydrocannabiphorol (THCP) and tetrahydrocannabivarin (TNCV).

68. The method for treating tissue of claim 46 wherein said formulation further comprises hemp.

69. The method for treating tissue of claim 46 wherein said formulation further comprises at least one additive selected from the group consisting of surfactants, emollients, lubricants, fragrances, colorants, flavorants, medications and natural oils.

70. The method for treating tissue of claim 69 wherein said formulation further comprises at least one additive selected from the group consisting of coconut oil, olive oil, monoglycerides, diglycerides and triglycerides.

* * * * *